United States Patent [19]
Mallion et al.

[11] 3,959,273
[45] *May 25, 1976

[54] MORPHOLINE DERIVATIVES

[75] Inventors: Keith Blakeney Mallion; Ralph William Turner; Alexander Henry Todd, all of Macclesfield, England

[73] Assignee: Imperial Chemical Industries Limited, London, England

[ * ] Notice: The portion of the term of this patent subsequent to Jan. 30, 1990, has been disclaimed.

[22] Filed: Sept. 27, 1974

[21] Appl. No.: 510,058

Related U.S. Application Data

[60] Division of Ser. No. 301,333, Oct. 27, 1972, Pat. No. 3,876,769, which is a continuation-in-part of Ser. No. 685,302, Nov. 24, 1967, Pat. No. 3,714,161.

[30] Foreign Application Priority Data
Dec. 28, 1966 United Kingdom.............. 57963/66

[52] U.S. Cl.......................... 260/247.7 S; 424/248; 260/247.1 R; 260/244 R
[51] Int. Cl.². ....................................... C07D 295/08
[58] Field of Search.............................. 260/247.7 S

[56] References Cited
UNITED STATES PATENTS
3,714,161  1/1973  Mallion........................ 260/247.7 S FOREIGN PATENTS OR APPLICATIONS
851,311   10/1960  United Kingdom.............. 260/247.7
1,138,405  1/1969  United Kingdom.............. 260/247.7

*Primary Examiner*—Harry I. Moatz
*Attorney, Agent, or Firm*—Cushman, Darby & Cushman

[57] ABSTRACT

The disclosure relates to new 2-aryloxymethylmorpholine derivatives which possess antidepressant properties, and to processes for the manufacture of the said morpholine derivatives, to pharmaceutical compositions containing them, and to a method of preventing or relieving depression in warm-blooded animals including man. Typical of the morpholine derivatives disclosed is 2-(o-ethoxyphenoxymethyl)morpholine.

2 Claims, No Drawings

MORPHOLINE DERIVATIVES

This is a division of application Ser. No. 301,333, filed Oct. 27, 1972, now U.S. Pat. No. 3,876,769, which in turn is a continuation-in-part of Ser. No. 685,302, filed Nov. 24, 1967, now U.S. Pat. No. 3,714,161.

This invention relates to morpholine derivatives.

According to the invention there is provided a morpholine derivative of the formula:

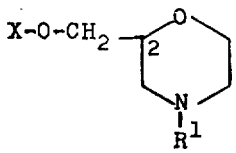

I wherein $R^1$ is hydrogen, alkyl of up to 3 carbon atoms, allyl or cyclopentyl, and wherein X is phenyl which is unsubstituted or which is substituted by one substituent selected from o-alkoxy of up to 7 carbon atoms, o-allyl, o-alkenyl, o-alkenyloxy or o-alkylthio each of up to 3 carbon atoms, o-chloro, o-phenoxy, o-hydroxy, p-methoxy or p-phenyl, or wherein X is 2,6-dimethoxyphenyl, naphthyl or tetrahydronaphthyl, and the non-toxic, pharmaceutically-acceptable acid-addition salts thereof.

It will be observed that the morpholine derivative of the invention possesses an asymmetric carbon atom (marked in 2 in the above formula) and the racemic form may therefore be resolved into two optically-active enantiomeric forms. The extent to which these enantiomers will possess the useful properties of the compounds of the invention, as hereafter defined, may differ, an it is therefore to be understood that this invention encompasses the racemic form of the morpholine derivative and any enantiomorphic form which possesses such a useful property.

A particular group of compounds of the invention are those of formula I wherein $R^1$ is hydrogen and wherein X is phenyl which is substituted by one substituent selected from o-alkoxy of up to 3 carbon atoms, o-methyl, o-allyl, o-allyloxy- o-chloro or o-phenyl, and the non-toxic, pharmaceutically-acceptable acid-addition salts thereof.

Particular new morpholine derivatives of the invention are 2-(o-ethoxyphenoxymethyl)morpholine; 2-(o-n-propoxyphenoxymethyl)morpholine; 2-(o-allylphenoxymethyl)morpholine; 2-(o-allyloxyphenoxymethyl)morpholine; and the non-toxic, pharmaceutically-acceptable acid-addition salts thereof.

The particularly preferred compound of the invention is 2-(o-ethoxyphenoxymethy)morpholine or a non-toxic, pharmaceutically-acceptable acid-addition salt thereof.

Suitable non-toxic, pharmaceutically-acceptable acid-addition salts of the morpholine derivative of the invention are salts derived from an inorganic or organic acid, for example hydrochlorides, hydrobromides, phosphates, sulphates, oxalates, lactates, tartrates, acetates, gluconates, salicylates or citrates.

The morpholine derivative of the invention may be manufactured by the reduction of a compound of the formula:

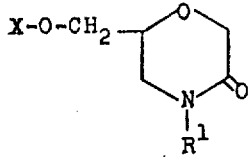

II wherein $R^1$ and X have the meanings stated above, with a complex metal hydride, whereafter if desired the product in free base form is reacted with an acid to form an acid-addition salt thereof. The complex hydride may be lithium aluminum hydride and the reduction may be carried out in an inert solvent and accelerated by the application of heat.

The starting material for the above process may be obtained by the reaction of a compound of the formula:

III wherein $R^1$ and X have the meanings stated above, with a compound of the formula $ZCH_2COZ^1$ wherein Z and $Z^1$, which may be the same or different, stand for halogen atoms, for example chlorine or bromine atoms, followed by cyclisation of the compound of the formula:

IV thus obtained. The compound of the formula III may itself be obtained as generally described in United Kingdom Pat. Nos. 994,918, 1,023,214 and 1,069,345.

The morpholine derivative in which $R^1$ stands for hydrogen may also be manufactured by replacement by hydrogen of the α-arylalkyl radical in a compound of the formula:

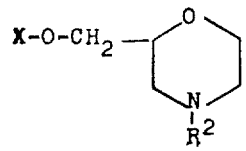

V wherein X is as above and $R^2$ is an α-arylalkyl radical. A suitable α-arylalkyl radical is the benzyl radical, and it may be replaced by hydrogen either by catalytic hydrogenolysis or by reaction with an alkyl chloroformate followed by alkaline hydrolysis of the alkoxycarbonyl derivative obtained as an intermediate.

The α-arylalkyl derivative used as starting material in the above process may be obtained by the reduction of the corresponding morpholine-5-one by a similar process to that described above for the manufacture of the morpholine derivative of the invention.

The compounds of the invention display antidepressant properties in man, and are therefore useful for the treatment or prophylaxis of depressive illness in man.

All clinically useful antidepressants have a calorigenic action in reserpinised mice, and this test is the one primarily used for establishing relative anti-depressant activity in a series of related compounds. The compounds of the invention all show activity on this test. The test (known as the RHL test) is carried out as follows:

Each member of various groups of 6 mice was given reserpine (2 mg. of base per kg. of bodyweight, given subcutaneously, as the phosphate). Seventeen hours later, the gastric temperature (To) of each mouse was recorded by means of an orally-inserted probe coupled to an electric thermometer which was calibrated in degrees Centigrade and which could be read to 0.05°C. Immediately after the temperature measurement, the mice were dosed orally with the test morpholine derivative or with saline (controls), each mouse in a group of 6 being given the same substance, and the gastric temperatures were again recorded at intervals of 2, 4 and 6 hours. The temperatures of the mice after these intervals were designated $T_2$, $T_4$ and $T_6$ respectively.

The effect of the morpholine derivative was computed from the mean cumulative rise in temperatures at the intervals of 2, 4 and 6 hours. The mean cumulative difference in temperature (C) is thus defined as the mean, calculated from the results obtained in 6 mice, of the sum:

$$T_2 + T_4 + T_6 - 3T_0$$

The effect of the morpholine derivative is related to the dose and, using suitable doses, a dose of morpholine derivative can be defined which gives a mean cumulative rise in temperature of 10°C. greater than that of control mice. This dose is called the $ED_{10}$, and the results obtained with various morpholine derivatives are as follows, the doses being recorded in mg. per kg. bodyweight.

The compounds tested have the formula:

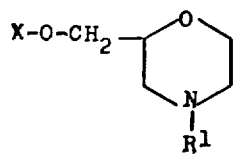

| X | $R^1$ | RHL $ED_{10}$ |
|---|---|---|
| phenyl | H | 3 |
| o-methoxyphenyl | H | 2 |
| o-ethoxyphenyl | H | 0.3 |
| o-ethoxyphenyl | isopropyl | 10 |
| o-ethoxyphenyl | allyl | 3–10 |
| o-propoxyphenyl | H | 0.3 |
| o-isopropoxyphenyl | H | 3 |
| o-heptyloxyphenyl | H | 3–10 |
| o-tolyl | H | 1–3 |
| o-allylphenyl | H | 0.3 |
| o-allyloxyphenyl | H | 0.3–1 |
| o-allyloxyphenyl | isopropyl | 3 |
| o-methylthiophenyl | H | <10 |
| o-chlorophenyl | H | 3 |
| o-chlorophenyl | isopropyl | <3 |
| o-phenoxyphenyl | H | 0.3 |
| o-hydroxyphenyl | H | <30 |
| p-methoxyphenyl | H | 10–30 |
| 4-biphenylyl | isopropyl | <10 |
| 2,6-dimethoxyphenyl | H | 10 |
| 1-naphthyl | H | 7 |
| 1-naphthyl | methyl | 10 |
| 1-naphthyl | isopropyl | 15 |
| 1-naphthyl | cyclopentyl | 10–30 |
| 5,6,7,8-tetrahydro-1-naphthyl | isopropyl | 10 |

One compound, 2-(o-ethoxyphenoxymethyl)morpholine, has been clinically tested and shown to be effective against clinically-diagnosed depression. The antidepressants in current clinical use are effective in about two thirds of all patients clinically diagnosed as suffering from depression, and the above compound has been found in clinical trials to be similarly effective. However, improvement in clinical condition is apparent very soon after the beginning of treatment with this compound.

According to a further feature of the invention, there is provided a pharmaceutical composition which comprises as active ingredient a minor amount of at least one morpholine derivative of the invention, in association with a major amount of a non-toxic, pharmaceutically-acceptable diluent or carrier therefor.

The pharmaceutical composition may be, for example, in a form suitable for oral or parenteral administration, for which purposes it may be formulated by means known to the art into the form of, for example, tablets, capsules, aqueous or oily solutions or suspensions, emulsions, sterile injectable aqueous or oily solutions or suspensions, or dispersible powders.

The pharmaceutical composition of the invention may also contain, in addition to the morpholine derivative or salt thereof, one or more known drugs selected from neuroleptic agents, for example chloropromazine, prochlorperazine, trifluoroperazine and haloperidol; other sedative drugs and tranquillizers, for example chlordiazepoxide, phenobarbitone and amylobarbitone; β-adrenergic blocking agents, for example propranolol; drugs used in the treatment of Parkinson's disease, for example benzhexol; and other antidepressant drugs, for example imipramine, desipramine, amitriptyline, nortriptyline, drugs of the amphetamine type and monoamineoxidase inhibitors, for example phenelzine and mebanazine.

A preferred pharmaceutical composition of the invention is one suitable for oral administration in unit dosage form, for example tablets and capsules, which contain between 20 and 200 mg. of active ingredient, or one suitable for intravenous or intramuscular injection, for example a sterile aqueous solution containing between 0.5 and 5% w/w of active ingredient.

The pharmaceutical composition of the invention will normally be administered to man for the treatment or prophylaxis of depressive illness, at such a dose that each patient receives a total oral dose of between 200 and 400 mg. of active ingredient per day, or a total intravenous or intramuscular dose of between 40 and 80 mg. per day, the composition being administered 2 to 4 times per day.

The invention is illustrated but not limited by the following Examples:

EXAMPLE 1

A mixture of 4-isopropyl-2-(naphth-1-yloxymethyl)-morpholin-5-one (20 g.), lithium aluminium hydride (5 g.) and ether (1 l.) is heated under reflux for 6 hours. The mixture is cooled, ethyl acetate (100 ml.) is added dropwise, and the mixture is then heated under reflux for 10 minutes. Water (1 l.) is added, and the organic phase is separated, washed with water and dried. A 1% ethereal solution of oxalic acid is added until precipitation of solid is complete, and the mixture is filtered. The solid residue is crystallised from butyl acetate and there is thus obtained 4-isopropyl-2-(naphth-1-yloxymethyl)morpholine hydrogen oxalate, m.p. 143°–145°C.

The 4-isopropyl-2-(naphth-1-yloxymethyl)morpholin-5-one used as starting material may be obtained as follows:

A solution of 1-isopropylamino-3-(naphth-1-yloxy)-2-propanol (75 g.) in ethylene chloride (1.5 l.) is added to a solution of sodium hydroxide (12 g.) in water (600 ml.). The mixture is cooled to −5°C. and is vigorously agitated to ensure thorough mixing of the two phases. Chloroacetyl chloride (25 ml.) is added dropwise during 30 minutes at such a rate that the temperature does not rise above 0°C., and the mixture is then stirred at ambient temperature for 3 hours. The organic phase is separated, washed with 10% aqueous hydrochloric acid and then with water, and is dried and evaporated to dryness.

A solution of the N-(2-hydroxy-3-naphth-1'-yloxypropyl)-N-isopropylchloroacetamide (86 g.) thus obtained as residue in methanol (1 l.) is added to a solution of sodium (6 g.) in methanol (1 l.) and the mixture is heated under reflux for 6 hours. The mixture is evaporated to dryness and the residue is shaken with ether (2 l.) and 10% aqueous hydrochloric acid (1 l.). The ethereal layer is separated, dried and evaporated to drynss and the residue is crystallised from petroleum ether (b.p. 80°–100°C.). There is thus obtained 4-isopropyl-2-(naphth-1-yloxymethyl)morpholin-5-one, m.p. 110.5°–111.5°C.

EXAMPLE 2

A mixture of 2-o-ethoxyphenoxymethyl-4-isopropylmorpholin-5-one (40 g.), lithium aluminium hydride (15 g.) and ether (2 l.) is heated under reflux for 6 hours. The mixture is cooled, ethyl acetate (100 ml.) is added dropwise, and the mixture is then heated under reflux for 10 minutes. Water (1 l.) is added, and the organic phase is separated, washed with water and dried. An ethereal solution of hydrogen chloride is added until precipitation of solid is complete, and the mixture is filtered. The solid residue is crystallised from butyl acetate and there is thus obtained 2-o-ethoxyphenoxymethyl-4-isopropylmorpholine hydrochloride, m.p. 158°–160°C.

The 2-o-ethoxyphenoxymethyl-4-isopropylmorpholin-5-one used as starting material may be obtained as follows:

A solution of cloroacetyl chloride (44 g.) in ether (500 ml.) is added gradually during 30 minutes to a stirred solution of 3-o-ethoxyphenoxy-1-isopropylamino-2-propanol (100 g.) and triethylamine (44 g.) in ether (4 l.). The mixture is stirred at ambient temperature for 24 hours and then filtered, and the filtrate is evaporated to dryness.

A solution of the N-(2-hydroxy-3-o-ethoxyphenoxypropyl)-N-isopropylchloroacetamide (133 g.) thus obtained in methanol (500 ml.) is added gradually during 30 minutes to a solution of sodium (9.3 g.) in methanol (2 l.). The mixture is heated under reflux for 6 hours and then evaporated to dryness. The residue is shaken with ether (1 l.) and 10% aqueous hydrochloric acid (500 ml.) and the organic phase is separated, washed with water, dried and evaporated to dryness. There is thus obtained 2-o-ethoxyphenoxymethyl-4-isopropylmorpholin-5-one as an oil.

EXAMPLE 3

A solution of 4-benzyl-2-(naphth-1-yloxymethyl)-morpholine (17.5 g.) and concentrated aqueous hydrochloric acid (0.5 ml.) in ethanol (400 ml.) is shaken with a 5% palladium-on-charcoal catalyst (7.5 g.) in an atmosphere of hydrogen at ambient temperature and atmospheric pressure until the uptake of hydrogen ceases. The mixture is filtered and the filtrate is evaporated to dryness. The residue is dissolved in ethyl acetate (100 ml.) and a solution of oxalic acid dihydrate (4 g.) in ethyl acetate (100 ml.) is added. The mixture is filtered and the solid residue is crystallised from a mixture of methanol and ethyl acetate. There is thus obtained 2-(naphth-1-yloxymethyl)morpholine hydrogen oxalate, m.p. 160°–162°C.

The 4-benzyl-2-(naphth-1-yloxymethyl)morpholine used as starting material may be obtained as follows:

A solution of chloroacetyl chloride (37 ml.) in methylene chloride (330 ml.) and a solution of triethylamine (33 ml.) in methylene chloride (330 ml.) are separately and simultaneously added during 30 minutes to a solution of 100 parts of 1-benzylamino-3-(naphth-1-yloxy)-2-propanol (100 g.) in methylene chloride (2 l.) which is stirred at a temperature of 0°C. The mixture is stirred at ambient temperature for 17 hours and is then washed successively with 10% aqueous hydrochloric acid (2.5 l.) and water (2.5 l.), dried and evaporated to dryness.

A solution of the N-benzyl-N-(2-hydroxy-3-naphth-1'-yloxypropyl)chloroacetamide (121 g.) thus obtained as residue in methanol (600 ml.) is added to a stirred solution of sodium (7.5 g.) in methanol (600 ml.) and the mixture is stirred and heated under reflux for 6 hours. The mixture is then stirred at ambient temperature for 16 hours and evaporated to dryness, and the residue is shaken with 10% aqueous hydrochloric acid (2.5 l.) and ether (2 l.). The organic phase is separated, washed with water, dried and evaporated to dryness. The residue is crystallised from petroleum ether (b.p. 100°–120°C.) and there is thus obtained 4-benzyl-2-(naphth-1-yloxymethyl)morpholin-5-one, m.p. 89.5°–91°C.

A suspension of lithium aluminium hydride (18 g.) in ether (700 ml.) is added gradually to a stirred suspension of 4-benzyl-2-(naphth-1-yloxymethyl)morpholin-5-one (54 g.) in ether (1070 ml.) and the mixture is then stirred and heated under reflux for 3 hours. Water (2 l.) is gradually added, and the organic phase is separated and extracted with a 10% aqueous hydrochloric acid (2 l.). The extract is made alkaline with 20% aqueous sodium hydroxide solution and the mixture is extracted with ethyl acetate. The extract is washed with water and dried, and ethereal hydrogen chloride solution is added until precipitation of solid is complete. The mixture is filtered and the solid residue is crystallised from methanol. There is thus obtained 4-benzyl-2-(naphth-1-yloxymethyl)morpholine hydrochloride, which melts between 170° and 230°C.

EXAMPLE 4

The process described in the last part of Example 3 is repeated except that 4-allyl-2-(naphth-1-yloxymethyl)-morpholin-5-one is used as starting material in place of 4-benzyl-2-(naphth-1-yloxymethyl)morpholin-5-one, and that ethereal oxalic acid solution is used in place of ethereal hydrogen chloride solution during the isolation procedure. The solid product is crystallised from methanol and there is thus obtained 4-allyl-2-(naphth-1-yloxymethyl)-morpholine hydrogen oxalate, m.p. 210°–212°C.

The 4-allyl-2-(naphth-1-yloxymethyl)morpholin-5-one used as starting material may be obtained as a solid, m.p. 112.5°–114°C. after crystallisation from petroleum ether (b.p. 100°–120°C.), by the procedure described in the second and third parts of Example 3 except that 1-allylamino-3-(naphth-1-yloxy)-2-propanol is used as starting material in place of 1-benzylamino-3-(naphth-1-yloxy)-2-propanol.

EXAMPLE 5

The process described in Example 4 is repeated except that 4-methyl-2-(naphth-1-yloxymethyl)morpholin-5-one is used as starting material in place of 4-allyl-2-(naphth-1-yloxymethyl)morpholin-5-one. The solid product is crystallised from a mixture of methanol and ethyl acetate and there is thus obtained 4-methyl-2-(naphth-1-yloxymethyl)morpholine hydrogen oxalate, m.p. 180°–182°C.

The 4-methyl-2-(naphth-1-yloxymethyl)morpholin-5-one used as starting material may be obtained as a solid, m.p. 105°–107°C. after crystallisation from petroleum ether (b.p. 100°–120°C.), by the procedure described in the second and third parts of Example 3 except that 1-methylamino-3-(naphthl-1-yloxy)-2-propanol (m.p. 94°–96°C., prepared from 1,2-epoxy-3-(naphth-1-yloxy)propane and methylamine) is used as starting material in place of 1-benzylamino-3-(naphth-1-yloxy)-2-propanol.

EXAMPLE 6

The process described in Example 3 is repeated except that the appropriate 4-benzyl-2-aryloxymethylmorpholine is used as starting material in place of 4-benzyl-2-(naphth-1-yloxymethyl)morpholine. There are thus obtained the compounds described in the following table:

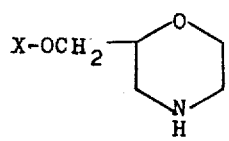

| X | Salt | m.p.(°C.) |
|---|---|---|
| 2-ethoxyphenyl | hydrogen oxalate | 106–108 |
| 2-methoxyphenyl | oxalate | 192–194 |
| 2-phenoxyphenyl | hydrogen oxalate | 158–160 |
| 2-tolyl | hydrogen oxalate | 117–120 |
| 2-n-propoxyphenyl | hydrogen oxalate | 133–135* |
| phenyl | hydrogen oxalate | 132–134 ** |
| 4-methoxyphenyl | hydrogen oxalate | 146–149.5 |
| 2,6-dimethoxyphenyl | hydrogen oxalate | 153–156 |
| 2-hydroxyphenyl | free base | 157–158 *** |
| 2-n-heptyloxyphenyl | hydrogen oxalate | 97–99 |

\* 2-(o-allyloxyphenoxymethyl)-4-benzylmorpholine used as starting material, the allyl radical being reduced to the n-propyl radical during hydrogenolysis.
\*\* 4-benzyl-2-(o-chlorophenoxymethyl)morpholine used as starting material, the chlorine atom being replaced by hydrogen during hydrogenolysis.
\*\*\* 4-benzyl-2-(o-benzyloxyphenoxymethyl)morpholine used as starting material, the benzyloxy radical being reduced to the hydroxy radical during hydrogenolysis.

The 4-benzyl-2-aryloxymethylmorpholine derivatives used as starting materials in the above process may be obtained by similar processes to those described in the second, third and fourth parts of Example 3, except that the appropriate 1-benzylamino-3-aryloxy-2-propanol derivatives are used as starting materials.

The 1-benzylamino-3-aryloxy-2-propanol derivatives themselves may be obtained by the condensation of the appropriate phenols with epichlorohydrin, followed by the interaction of the products thus obtained with benzylamine. Some of the said 1-benzylamino-3-aryloxy-2-propanol derivatives are known compounds, and some of them have not been characterised. 1-Benzylamino-3-(o-ethoxyphenoxy)-2-propanol has m.p. 77°–79°C. and 1-benzylamino-3-(o-allyloxyphenoxy)-2-propanol has m.p. 87°–90°C.

EXAMPLE 7

A solution of 2-(o-allyloxyphenoxymethyl)-4-isopropylmorpholin-5-one (10.4 g.) in dry ether (100 ml.) is added gradually to a stirred suspension of lithium aluminium hydride (1.4 g.) in dry ether (150 ml.), and the mixture is stirred and heated under reflux for 3 hours, and then stirred for a further 14 hours at ambient temperature. Water (15 ml.) is gradually added, and the organic phase is separated and extracted with 10% aqueous hydrochloric acid (200 ml.). The acidic extract is made alkaline with 45% aqueous sodium hydroxide solution and the mixture is extracted with ethyl acetate. The organic extract is washed with water, dried and evaporated to dryness. The residue is dissolved in ethyl acetate (10 ml.), and a solution of oxalic acid dihydrate (2.5 g.) in ethyl acetate (10 ml.) is added. The mixture is filtered and the solid residue is crystallised from a mixture of methanol and ethyl acetate. There is thus obtained 2-(o-allyloxyphenoxymethyl)-4-isopropylmorpholine hydrogen oxalate, m.p. 132°–134°C.

The 2-(o-allyloxyphenoxymethyl)-4-isopropylmorpholin-5-one used as starting material may be obtained as follows:

A solution of chloroacetyl chloride (4.5 ml.) in methylene chloride (25 ml.) and a solution of triethylamine (4.3 ml.) in methylene chloride (25 ml.) are separately and simultaneously added during 30 minutes to a stirred solution of 3-(o-allyloxyphenoxy)-1-isopropylamino-2-propanol (11 g.) in methylene chloride (150 ml.). The mixture is stirred at ambient temperature for 17 hours, and is then washed successively with 10% aqueous hydrochloric acid (200 ml.) and water (200 ml.) dried, and evaporated to dryness.

A solution of the N-[2-hydroxy-3-(o-allyloxyphenoxy)propyl]-N-isopropylchloroacetamide (12.6 g.) thus obtained as residue in dry methanol (75 ml.) is added to a stirred solution of sodium (1.48 g.) in dry methanol (75 ml.), and the mixture is stirred and heated under reflux for 6 hours. The mixture is then stirred at ambient temperature for 11 hours and evaporated to dryness, and the residue is shaken with 10% aqueous hydrochloric acid (200 ml.) and ethyl acetate (200 ml.). The organic phase is separated, washed with water, dried and evaporated to dryness. There is thus obtained 2-(o-allyloxyphenoxymethyl)-4-isopropylmorpholin-5-one as an oil.

EXAMPLE 8

The process described in Example 7 is repeated except that the appropriate 2-aryloxymethylmorpholin-5-one is used as starting material in place of 2-(o-allyloxyphenoxymethyl)-b 4-isopropylmorpholin-5-one. There are thus obtained the compounds described in the following table:

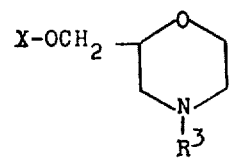

| X | R³ | m.p. (°C.) of hydrogen oxalate salt |
|---|---|---|
| 2-allyloxyphenyl | hydrogen | 115–118 |
| 1-naphthyl | cyclopentyl | 163–165 |
| 5,6,7,8-tetrahydro-1-naphthyl | isopropyl | 166–168 |
| 2-ethoxyphenoxy | allyl | 128–129 |
| 4-biphenyl | isopropyl | 180–181 |
| 2-chlorophenyl | isopropyl | 117–118 |
| 2-isopropoxyphenyl | hydrogen | 96–103 (contains one molecule of methanol of crystallisation) |

The 2-aryloxymethylmorpholin-5-one derivatives used as starting materials in the above process may be obtained by similar processes to those described in the second and third parts of Example 7, except that the appropriate 1-amino-3-aryloxy-2-propanol derivatives are used as starting materials.

The 1-amino-3-aryloxy-2-propanol derivatives themselves may be obtained by the condensation of the appropriate phenols with epichlorohydrin, followed by the interaction of the products thus obtained with ammonia or with the appropriate amines. 3-(o-Allyloxyphenoxy)-1-amino-2-propanol has m.p. 57°–60°C.

EXAMPLE 9

Ethyl chloroformate (0.33 ml.) is added to a solution of 4-benzyl-2-(2-ethoxyphenoxymethyl)morpholine (1.0 g.) in benzene (20 ml.) and the mixture is heated under reflux for 17 hours, and then evaporated to dryness. The residue is dissolved in methanol (10 ml.) and the solution is added to a solution of potassium hydroxide (2 g.) in methanol (30 ml.). The mixture is heated under reflux for 24 hours, and then evaporated to dryness. The residue is shaken with 10% aqueous hydrochloric acid (100 ml.) and ether (100 ml.) and the aqueous phase is separated, made alkaline with 45% aqueous sodium hydroxide solution, and extracted with ether (100 ml.). The ethereal extract is washed with water, dried, and evaporated to dryness. The residue is dissolved in ether (10 ml.) and the solution is added to a solution of acetic acid (0.3 ml.) in ether (10 ml.). The mixture is filtered and the solid residue is crystallised from a mixture of methanol and ether. There is thus obtained 2-(2-ethoxyphenoxymethyl)morpholine acetate, m.p. 111°–114°C.

The process described above is repeated except that 4-benzyl-2-(o-chlorophenoxymethyl)morpholine is used as starting material in place of 4-benzyl-2-(o-ethoxyphenoxymethyl)-morpholine, and that oxalic acid is used in place of acetic acid. There is thus obtained 2-(o-chlorophenoxymethyl)-morpholine hydrogen oxalate, m.p. 144°–147°C.

The process described above is repeated except that 4-benzyl-2-(o-methylthiophenoxymethyl)morpholine (prepared by processes similar to those generally described in Examples 3 and 6 from o-methylthiophenol) is used as starting material in place of 4-benzyl-2-(o-ethoxyphenoxymethyl)morpholine, and that oxalic acid is used in place of acetic acid. There is thus obtained 2-(o-methylthiophenoxymethyl)morpholine hydrogen oxalate.

The process described above is repeated except that 4-benzyl-2-(o-allylphenoxymethyl)morpholine (prepared by processes similar to those generally described in Examples 3 and 6 from o-allylphenol) is used as starting material in place of 4-benzyl-2-(o-ethoxyphenoxymethyl)-morpholine, and that oxalic acid is used in place of acetic acid. There is thus obtained 2-(o-allylphenoxymethyl)morpholine hydrogen oxalate, m.p. 87°–94°C.

EXAMPLE 10

2-(o-Ethoxyphenoxymethyl)morpholine hydrochloride (23.0 g.), lactose (146 g.) and maize starch (25.0 g.) are mixed together and an aqueous solution of gelatin (10% w/v; 40 ml.) is added with mixing to produce a mass suitable for granulation. The mixture is passed through a No. 20 mesh screen and the resultant granules are dried at a temperature not exceeding 60°C. Magnesium stearate (2.0 g.) is incorporated and the granules are passed through a No. 30 mesh screen, remixed and compressed into 200 mg. tablets each containing 20 mg. of 2-(o-ethoxyphenoxymethyl)morpholine.

EXAMPLE 11

2-(o-Ethoxyphenoxymethyl)morpholine hydrochloride (11.5 g.), maize starch (19 g.), calcium phosphate (10 g.), 'Avicel' (10 g.) and 'Primojel' (8 g.) are mixed together and granulated with maize starch (2 g.) made up as a 7½ % aqueous paste. The wet mass is passed through a No. 12 mesh screen and the granules are dried at a temperature not exceeding 60°C. and resieved through a No. 20 mesh screen. Magnesium stearate (3 g.) and Avicel (30 g.) are added, the whole blended together and the final blend compressed into 300 mg. tablets each containing 100 mg. of 2-(o-ethoxyphenoxymethyl)morpholine.

'Avicil' is a microcrystalline cellulose available from F.M.C. Corp., U.S.A.

'Primojel' is a sodium starch glycollate available from W. A. Scholten's Chemische Fabrieken N.V., Foxhol (Gr), Netherlands.

EXAMPLE 12

Citric and B.P. (0.5 g.) is dissolved in water for injection (75 ml.) and 2-(o-ethoxyphenoxymethyl)morpholine hydrochloride (2.36 g.) is added slowly to this solution with stirring. The pH of the solution is adjusted to 5.0 with N/l sodium hydroxide solution, the volume is made up to 100 ml. with water for injection and the pH is rechecked. The solution is filtered through a 5μ millipore membrane, distributed into 1 ml. ampoules and sterilized by autoclaving at 121°C. for 20 minutes. There is thus obtained a 2.0% solution of 2-(o-ethoxyphenoxymethyl)morpholine suitable for injection.

EXAMPLE 13

Fourteen clinically-depressed patients were rated on day 0 for degree of mental depression using a modified Hamilton Scale (Hamilton, J. Neurol. Neurosurg. Psychiat., 1960, 23, 56). The check list used to establish the rating was as follows:

HAMILTON PSYCHIATRIC RATING SCALE FOR DEPRESSION

Patient's Name:  Patient's No.:
Project:  Rater:  Date:

FOR EACH ITEM SELECT THE "CUE" WHICH BEST CHARACTERIZES THE PATIENT    Check    Card Col.

| | | Check | Card Col. |
|---|---|---|---|
| 1. DEPRESSED MOOD (Sadness, hopeless, helpless, worthless) | Absent | ( ) | 0 |
| | These feeling states indicated only on questioning | | 1 |
| | These feeling states spontaneously reported verbally | | 2 |
| | Communicates feeling states non-verbally — i.e. through facial expression, posture, voice, and tendency to weep | | 3 |
| | Patient reports VIRTUALLY ONLY these feeling states in his spontaneous verbal and non-verbal communication | | 4 |
| 2. FEELINGS OF GUILT | Absent | ( ) | 0 |
| | Self-reproach, feels he has let people down | | 1 |
| | Ideas of guilt or rumination over past errors or sinful deeds | | 2 |
| | Present illness is a punishment. Delusions of guilt | | 3 |
| | Hallucinations of guilt | | 4 |
| 3. SUICIDE | Absent | ( ) | 0 |
| | Feels life is not worth living | | 1 |
| | Wishes he were dead or any thoughts of possible death to self | | 2 |
| | Suicide ideas or gesture | | 3 |
| | Attempts at suicide (any serious attempt rates 4) | | 4 |
| 4. INSOMNIA-EARLY | No difficulty falling asleep | ( ) | 0 |
| | Complains of occasional difficulty falling asleep — i.e. more than ½ hour | | 1 |
| | Complains of nightly difficulty falling asleep | | 2 |
| 5. INSOMNIA-MIDDLE | No difficulty | ( ) | 0 |
| | Patient complains of being restless and disturbed during the night | | 1 |
| | Waking during the night — Any getting out of bed rates 2 (except for purpose of voiding) | | 2 |
| 6. INSOMNIA-LATE | Sleeps until awakened by staff | ( ) | 0 |
| | Waking in early hours of the morning but goes back to sleep | | 1 |
| | Unable to fall asleep again if gets out of bed | | 2 |
| 7. WORK AND ACTIVITIES | No difficulty | ( ) | 0 |
| | Thoughts and feelings of incapacity, fatigue or weakness related to activities, work or hobbies | | 1 |
| | Loss of interest in activity, hobbies or work — either directly reported by patient, or indirect in listlessness, indecision and vacillation (feels he has to push self to work or activities | | 2 |
| | Decrease in actual time spent in activities or decrease in productivity. In hospital, rate 3 if patient does not spend at least three hours a day in activities (hospital job or hobbies) exclusive of ward chores | | 3 |
| | Stopped working because of present illness. In hospital, rate 4 if patient engages in no activities except ward chores, or if patient fails to perform ward chores unassisted | | 4 |
| 8. RETARDATION (Slowness of thought and speech; impaired ability to concentrate; decreased motor activity) | Normal speech and thought | ( ) | 0 |
| | Slight retardation at interview | | 1 |
| | Obvious retardation at interview | | 2 |
| | Interview difficult | | 3 |
| | Complete stupor | | 4 |
| 9. AGITATION | None | ( ) | 0 |
| | "Playing with" hands, hair, etc. | | 1 |
| | Hand-wringing, nail-biting, hair pulling, biting of lips | | 2 |
| 10. ANXIETY-PSYCHIC | No difficulty | ( ) | 0 |
| | Subjective tension and irritability | | 1 |
| | Worrying about minor matters | | 2 |
| | Apprehensive attitude apparent in face or speech | | 3 |
| | Fears expressed without questioning | | 4 |
| 11. ANXIETY-SOMATIC | Physiological concomitants of anxiety, such as: Gastro-intestinal — dry mouth, wind, indigestion, diarrhoea, cramps, belching Cardio-vascular — palpitations, headaches Respiratory — hyperventilation, sighing Urinary frequency Sweating | Rate severity of any or all 0 – 4 | ( ) |
| | heap of garbage" or its equivalent | Write in rating | 4 |

-continued
HAMILTON PSYCHIATRIC RATING SCALE FOR DEPRESSION

Patient's Name:  Patient's No.:
Project:  Rater:  Date:

FOR EACH ITEM SELECT THE "CUE" WHICH BEST CHARACTERIZES THE PATIENT    Check    Card Col.

| | | | | |
|---|---|---|---|---|
| | | None | in last column | ( )<br>0 |
| 12. | SOMATIC SYMPTOMS GASTRO-INTESTINAL | Loss of appetite but eating without staff encouragement. Heavy feelings in abdomen | | 1 |
| | | Difficulty eating without staff urging. Regests or requires laxative or medication for bowels or medication for G.I. symptoms | | 2 |
| | | None | | ( )<br>0 |
| 13. | SOMATIC SYMPTOMS GENERAL | Heaviness in limbs, back or head. Backache, headache, muscle aches. Loss of energy and fatiguability | | 1 |
| | | Any clear-cut symptom rates 2 | | 2 |
| | | If inadequate information known to rate this item, | Rate | ( ) |
| 14. | GENITAL SYMPTOMS | score 1<br>Disturbance of sexuality<br>Menstrual disturbances | 0 – 2<br>Write in<br>rating | |
| | | Not present | | ( )<br>0 |
| | | Self-absorption (bodily) | | 1 |
| 15. | HYPOCHONDRIASIS | Preoccupation with health | | 2 |
| | | Frequent complaints, requests for help, etc. | | 3 |
| | | Hypochondriacal delusions | | 4 |
| | | A. WHEN RATING BY HISTORY: | | ( ) |
| | | No weight loss | | 0 |
| | | Probable weight loss associated with present illness | | 1 |
| 16. | LOSS OF WEIGHT | Definite (according to patient) weight loss | | 2 |
| | | B. ON WEEKLY RATINGS BY WARD PSYCHIATRIST, WHEN ACTUAL WEIGHT CHANGES ARE MEASURED | | |
| | | Less than 1 lb. weight loss in week | | 0 |
| | | Greater than 1 lb. weight loss in week | | 1 |
| | | Greater than 2 lb. weight loss in week | | 2 |
| | | Acknowledges being depressed and ill | | ( )<br>0 |
| 17. | INSIGHT | Acknowledges illness but attributes cause to bad food, climate, overwork, virus, need for rest etc. | | 1 |
| | | Denies being ill at all | | 2 |
| | | If symptoms are worse | morning  Rate 0 – 2 | ( ) |
| 18. | DIURNAL VARIATION | in morning or evening note which it is and rate severity of variation | evening  Write in rating | |
| 19. | DEPERSONALIZATION AND DEREALIZATION | Specify:<br>Feelings of unreality<br>Nihilistic ideas | Rate severity 0 – 4<br><br>Write in rating | ( ) |
| | | None | | ( )<br>0 |
| | | Suspicious | | 1–2 |
| 20. | PARANOID SYMPTOMS | Ideas of reference | | 3 |
| | | Delusions of reference and persecution | | 4 |
| 21. | OBSESSIONAL & COMPULSIVE SYMPTOMS | Obsessive thoughts and compulsive acts against which the patient struggles | Rate 0 – 2<br>Write in rating | ( ) |
| | | Not present | | ( )<br>0 |
| 22. | HELPLESSNESS | Subjective feelings which are elicited only by inquiry. Patient volunteers his helpless feelings | | 1<br>2 |
| | | REQUIRES urging, guidance and reassurance to accomplish ward chores or personal tasks | | 3 |
| | | Requires physical assistance for dress, grooming, eating, bedside tasks or personal hygiene | | 4 |
| | | Not present | | ( )<br>0 |
| | | Intermittently doubts that "things will improve" but can be reassured | | 1 |
| 23. | HOPELESSNESS | Consistently feels "hopeless" but accepts reassurances | | 2 |
| | | Expresses feelings of discouragement, despair, pessimism about future, which cannot be dispelled | | 3 |
| | | Spontaneously and inappropriately perseverates, "I'll never get well" or its equivalent | | 4 |
| | | Not present | | ( )<br>0 |
| 24. | WORTHLESSNESS (Ranges from mild loss of esteem, feelings of inferiority, self-depreciation to delusional notions of worthlessness) | Indicates feelings of worthlessness (loss of self-esteem) only on questioning | | 1 |
| | | Spontaneously indicates feelings of worthlessness (loss of self-esteem) | | 2 |
| | | Different from 2 by degree: Patient volunteers that he is "no good", "inferior" etc. | | 3 |
| | | Delusional notions of worthlessness — i.e. "I am a | | |

The patients were then dosed 4 times per day for 21 days with 100 mg. of 2-(o-ethoxyphenoxymethyl)morpholine, either in a double blind or open situation, and their Hamilton Ratings were measured at regular intervals throughout the 21 days. The results were as follows:

| Patient No. | Type of Trial | Initial Rating | 7-Day Rating | 21-Day Rating |
|---|---|---|---|---|
| 1 | d.b. | 11 | 14 | 16 |
| 2 | d.b. | 24 | 25 | 24 |
| 3 | d.b. | 10 | 5 | 3 |
| 4 | d.b. | 22 | 10 | 3 |
| 5 | d.b. | 12 | 13 | 2 |
| 6 | d.b. | 27 | 20 | 19 |
| 7 | o | 21 | 29 | 21 |
| 8 | o | 8 | 14 | 18 |
| 9 | o | 13 | 13 | 2 |
| 10 | o | 16 | 6 | 4 |
| 11 | o | 19 | 10 | 5 |
| 12 | o | 12 | 33 | 33 |
| 13 | o | 23 | 14 | 0 |
| 14 | o | 27 | 22 | 22 | d.b. = double blind
o = open

It can be seen that nine of the fourteen patients showed a positive response, as measured by a significant fall in Hamilton Rating, after 21 days treatment, and of these, seven already showed this response after only seven days treatment.

EXAMPLE 14

Nine clinically-depressed patients in an open trial were rated on day 0 for degree of mental depression on the modified Hamilton Scale as in Example 13. They were then dosed with 2-(o-ethoxyphenoxymethyl)morpholine at a dose of 100 mg. twice a day for 7 days, 100 mg. 3 times a day for a further 7 days and 100 mg. 4 times a day for yet a further 7 days and their Hamilton Ratings were measured at intervals. The results were as follows:

| Patient No. | Length of Trial (Days) | Initial Rating | Final Rating |
|---|---|---|---|
| 15 | 21 | 31 | 6 |
| 16 | 21 | 38 | 0 |
| 17 | 12 | 27 | 28 |
| 18 | 17 | 27 | 21 |
| 19 | 16 | 22 | 6 |
| 20 | 7 | 20 | 19 |
| 21 | 21 | 27 | 0 |
| 22 | 8 | 21 | 27 |
| 23 | 12 | 18 | 17 |

It can be seen that five of the nine patients showed a positive response, as measured by a significant fall in Hamilton Rating. The time course of the response is illustrated in the following graph in which the percentage change in Hamilton Rating is plotted against time. The rapid onset of action of the drug in those patients who responded is readily apparent.

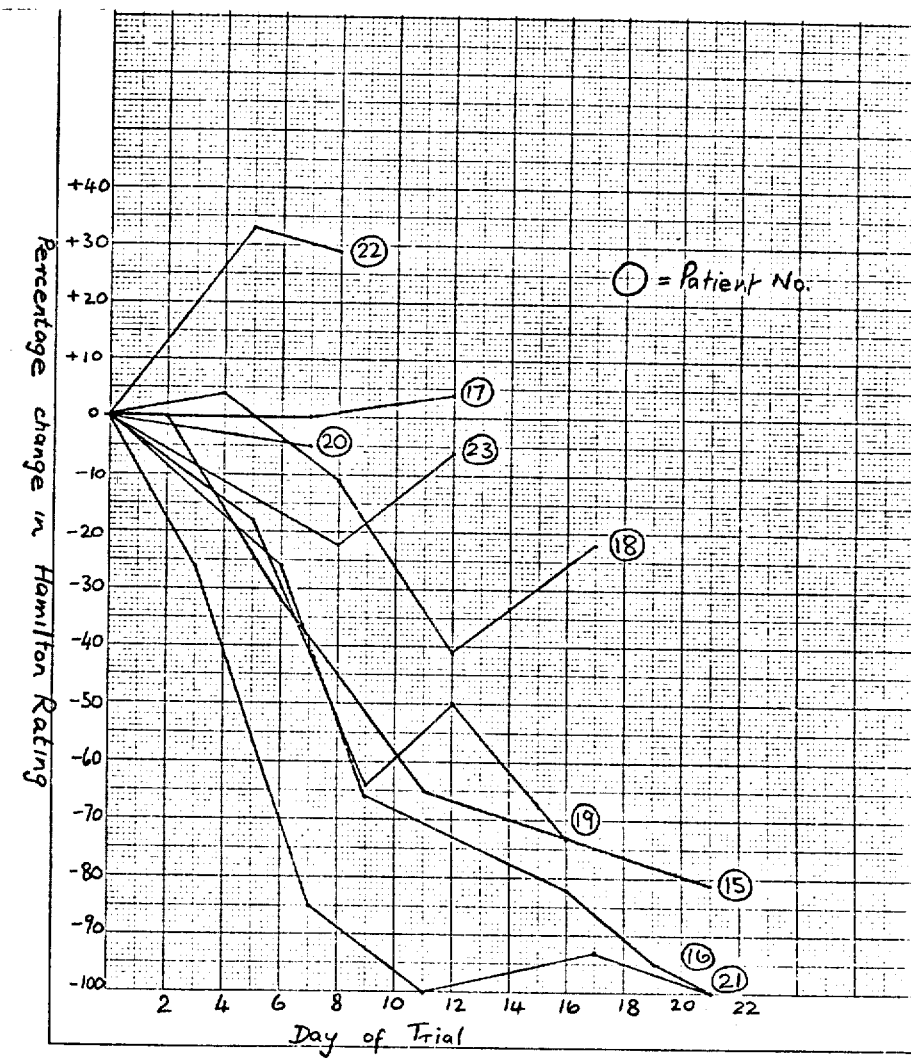

What we claim is:
1. A morpholine selected from compounds of the formula:

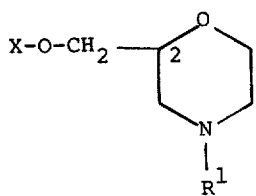

wherein $R^1$ is hydrogen and wherein X is phenyl which is substituted by one substituent selected from o-alkoxy of up to 3 carbon atoms, o-methyl, o-allyl, o-allyloxy, o-chloro or o-phenyl, and the non-toxic, pharmaceutically-acceptable acid-addition salts thereof.

2. A compound, as claimed in claim 1, which is selected from 2-(o-n-propoxyphenoxymethyl)morpholine; 2-(o-allylphenoxymethyl)morpholine; 2-(o-allyloxyphenoxymethyl)morpholine; and 2-(o-phenoxyphenoxymethyl)morpholine and the non-toxic, pharmaceutically-acceptable acid-addition salts thereof.

* * * * *